(12) United States Patent
Harradine et al.

(10) Patent No.: US 6,514,416 B1
(45) Date of Patent: Feb. 4, 2003

(54) METHOD AND APPARATUS FOR MAGNETIC SEPARATION OF PARTICLES

(75) Inventors: Mark A. Harradine, Mountain View, CA (US); Richard V. Bennett, Dublin, CA (US)

(73) Assignee: Dexter Magnetic Technologies, Inc., Fremont, CA (US)

(*) Notice: Subject to any disclaimer, the term of this patent is extended or adjusted under 35 U.S.C. 154(b) by 9 days.

(21) Appl. No.: 09/850,872

(22) Filed: May 7, 2001

(51) Int. Cl.[7] .................. B01D 35/06; G01N 33/553
(52) U.S. Cl. .................. 210/695; 210/222; 422/104; 435/173.1; 436/526
(58) Field of Search .................. 210/222, 695; 422/104; 435/173.1; 436/526

(56) References Cited

U.S. PATENT DOCUMENTS

| | | |
|---|---|---|
| 4,988,618 A | 1/1991 | Li et al. |
| 5,466,574 A | 11/1995 | Liberti et al. |
| 5,567,326 A | 10/1996 | Ekenberg et al. |
| 5,779,907 A | 7/1998 | Yu |

Primary Examiner—David A. Reifsnyder
(74) Attorney, Agent, or Firm—Blakely Sokoloff Taylor & Zafman, LLP (57) ABSTRACT

A method and apparatus for magnetic separation of particles within a container. In one embodiment, a plurality of magnets are arranged in a first row and in a second row on a frame, wherein the plurality of magnets are oriented in a plane coplanar with a horizontal cross sectional plane of the frame. The frame has housing means between the first row and the second row for housing containers. The plurality of magnets apply north-south magnetic fields oriented coplanar with the horizontal cross sectional plane of the frame. The north-south magnetic field direction of a first magnet in the first row alternates 180 degrees from the north-south magnetic field direction of a second magnet in the first row, and the north-south magnetic field direction of a first magnet in the second row opposes the north-south magnetic field direction of the first magnet in the first row.

24 Claims, 7 Drawing Sheets

METHOD AND APPARATUS FOR MAGNETIC SEPARATION OF PARTICLES

FIELD OF INVENTION

The present invention generally relates to the use of magnetic fields. More specifically, the present invention relates to the magnetic separation of particles in a solution.

BACKGROUND OF THE INVENTION

Laboratories often require a technique to separate particles in a solution. Target particles, such as proteins and the like, may be separated from a solution by a technique known as magnetic separation.

In general, magnetic separation of biological particles, such as target proteins, involves coating small magnetically susceptible paramagnetic or ferromagnetic materials, such as micro-beads with a chemical-specific substance that is known to chemically bond with the target proteins. The coated micro-beads are introduced into a well containing a solution of the target proteins and unwanted biological molecules. The target proteins chemically bond to the coating of the micro-beads. Magnets are placed near the well to apply magnetic fields in the well and the solution.

The micro-beads, including the target proteins chemically bonded to the coating of the micro-beads, are attracted to the magnets in accord with the direction and strength of the magnetic fields generated by the magnets. Placement of the magnets determines where in the well the micro-beads with the target proteins will collect, i.e., if the magnets are placed along the side of the well, the micro-beads will collect to the side wall of the well. Once the micro-beads have been collected at the desired location, the well is rinsed, removing the solution and unwanted particles. The collected micro-beads with the target proteins chemically bonded to the coating of the micro-beads remain in the well as long as the magnetic fields are applied.

Once the well has been rinsed, a "clean" solution, without unwanted particles, is introduced into the well. A chemical is mixed with the "clean" solution to break the chemical bonds between the target proteins and the coating of the micro-beads, resulting in a well with isolated target proteins. Additionally, the micro-beads may be removed by disabling/removing the magnetic fields from the well.

Molecular biological magnetic separation is well known, and until relatively recently, this process was performed using large tubes of fluids (e.g., 15–50 ml tubes) and micro-beads. Recent molecular magnetic separation techniques typically involve the use of 96-well micro-plates, that is, a tray having 96 wells, arranged in an 8×12 matrix, with each well capable of holding 250–500 micro-liter ($\mu$l) of liquid. A variety of placement methods for magnets to apply the desired magnetic fields may be employed on these micro-plates. One method is to place small magnets, having predetermined magnetic fields, between micro-plate receiving orifices, so that the micro-beads collect along the walls of the wells as described by Li, et al., U.S. Pat. No. 4,988,618. Another method is to place an apparatus with magnetic pins into the wells with the micro-beads collecting on the pins as described by Ekenberg, et. al., U.S. Pat. No. 5,567,326. Another method is to have a base for a micro-plate with cylindrical magnets positioned for insertion from the base of the micro-plate into the spaces between the wells of the micro-plate with the micro-beads collecting along the walls of the wells as described by Yu, U.S. Pat. No. 5,779,907.

As molecular magnetic separation techniques advance the number of wells increase. In high throughput applications, typically involving automated systems, 384-well to 1536-well micro-plates are utilized to increase capacity and throughput. In such systems, each 384-well micro-plate is arranged as 16×24 wells, while each 1536-well micro-plate is arranged as 32×48 wells, effectively increasing the volume of the conventional 96-well micro-plate by 4 and 16 times respectively.

As the number of wells increase, the spaces between the individual wells in micro-plates are relatively small, making the magnetic separation methods of Li, Ekenberg, and Yi difficult, if not impracticable. However, magnets are still required to separate the target particles from the solution contained in micro-plates.

BRIEF DESCRIPTION OF THE DRAWINGS

The present invention is illustrated by way of example and not by way of limitation in the figures of the accompanying drawings, in which the like references indicate similar elements and in which.

DETAILED DESCRIPTION OF THE INVENTION

Described is a method and apparatus that significantly increases the strength of the magnetic fields within micro-plate wells and hence significantly increases the throughput for micro-bead separation. In the following description, various aspects of the present invention will be described. However, it will be apparent to those skilled in the art that the present invention may be practiced with only some or all aspects of the present invention. For purposes of explanation, specific numbers, materials and configurations are set forth in order to provide a thorough understanding of the present invention. However, it will also be apparent to one skilled in the art that the present invention may be practiced without the specific details. In other instances, well known features are omitted or simplified in order not to obscure the present invention.

Various operations will be described as multiple discrete steps in turn, in a manner that is most helpful in understanding the present invention. However, the order of description should not be construed as to imply that these operations are necessarily order dependent. In particular, these operations need not be performed in the order of presentation.

Figure 1:
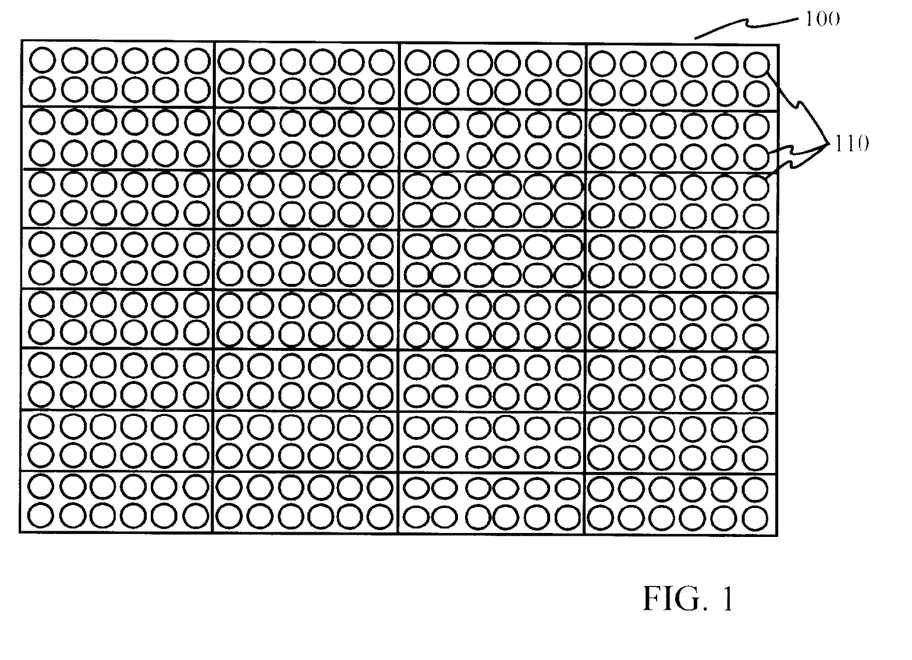
FIG. 1 illustrates a micro-plate upon which the invention may be practiced.

FIG. 1 illustrates a micro-plate upon which the invention may be practiced. FIG. 1 is a plan view of a 384-well micro-plate 100 having wells 110 arranged in a 16×24 configuration. According to one example implementation, each of the wells 110 is capable of holding 250–500 µl of liquid. Although the wells illustrated are substantially circular, other geometric shapes are contemplated, for example, substantially square or even oval wells may be utilized. In FIG. 1 a 384-well micro-plate is shown, however, it should be appreciated by one skilled in the art that the teachings of the present invention may be practiced upon a wide range of containers used for magnetic separation of materials such as, but not limited to, 96-well micro-plates, 1536-well micro-plates, tubes, Petri dishes, pipettes, beakers, and bottles each container comprising various shapes and dimensions.

Figure 2:
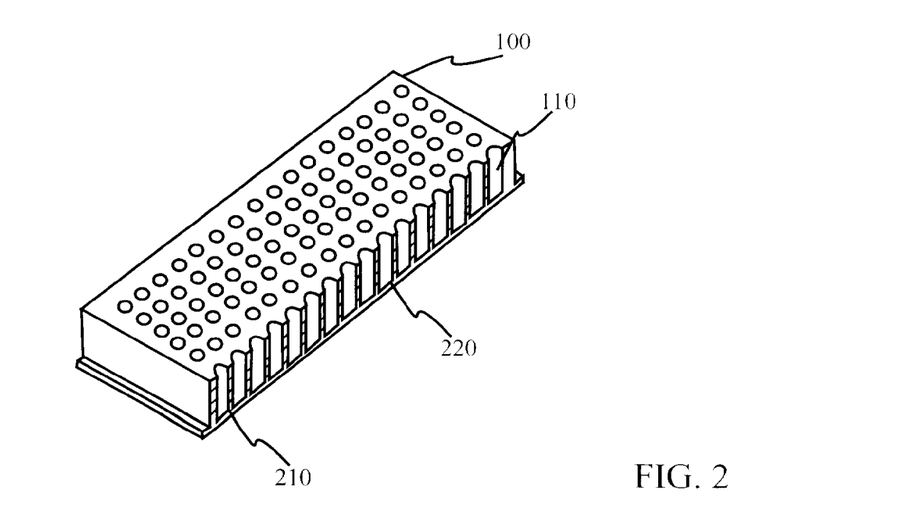
FIG. 2 illustrates a perspective view of a micro-plate.

FIG. 2 illustrates a perspective view of a micro-plate 100. As shown in FIG. 2, because of tightly packed density of wells, the placing of magnets with conventional shapes, i.e., square, rectangular, or circular within spaces 210 around the periphery of the wells 110 create magnetic fields that are relatively weak. These relatively weak magnetic fields decrease the throughput for micro-bead separation.

Figure 3:
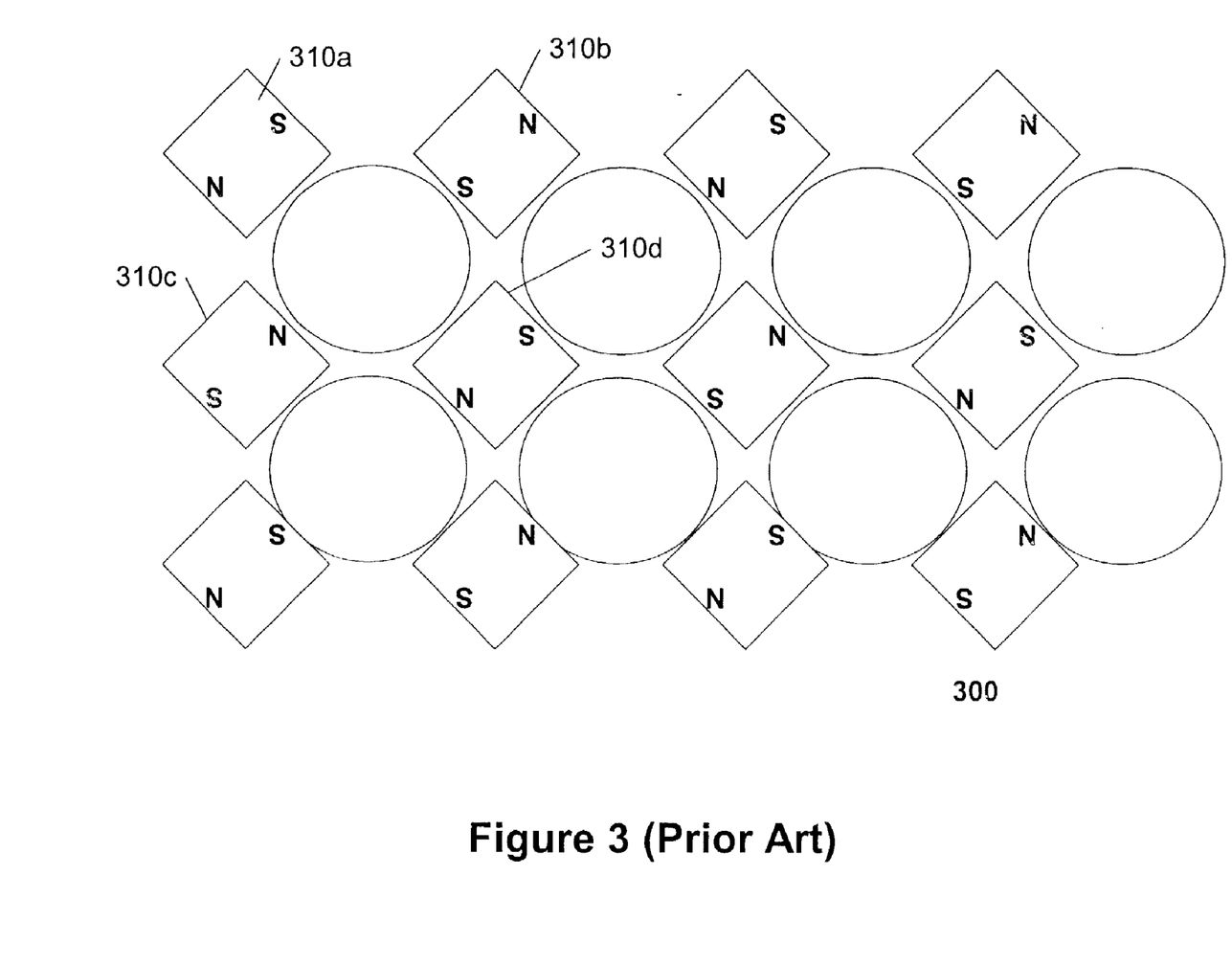
FIG. 3 illustrates a plan view of a prior art embodiment for separation of particles in containers.

FIG. 3 illustrates a plan view of a prior art embodiment for an arrangement of magnets 300 facilitating separation of particles in a well. In FIG. 3, four square shaped permanent magnets 310a–d are evenly spaced around the periphery of a well. Each square shaped permanent magnet has a north-south magnetic field that is coplanar with a transverse cross section of the plane of the wells. Due to the orientation of the north-south magnetic fields, micro-beads are accumulated in the well, in the four regions proximate the poles of the magnets. However, the magnetic fields created as a result of this arrangement of magnets are relatively weak, therefore, the throughput for micro-bead separation is significantly reduced.

Figure 4:
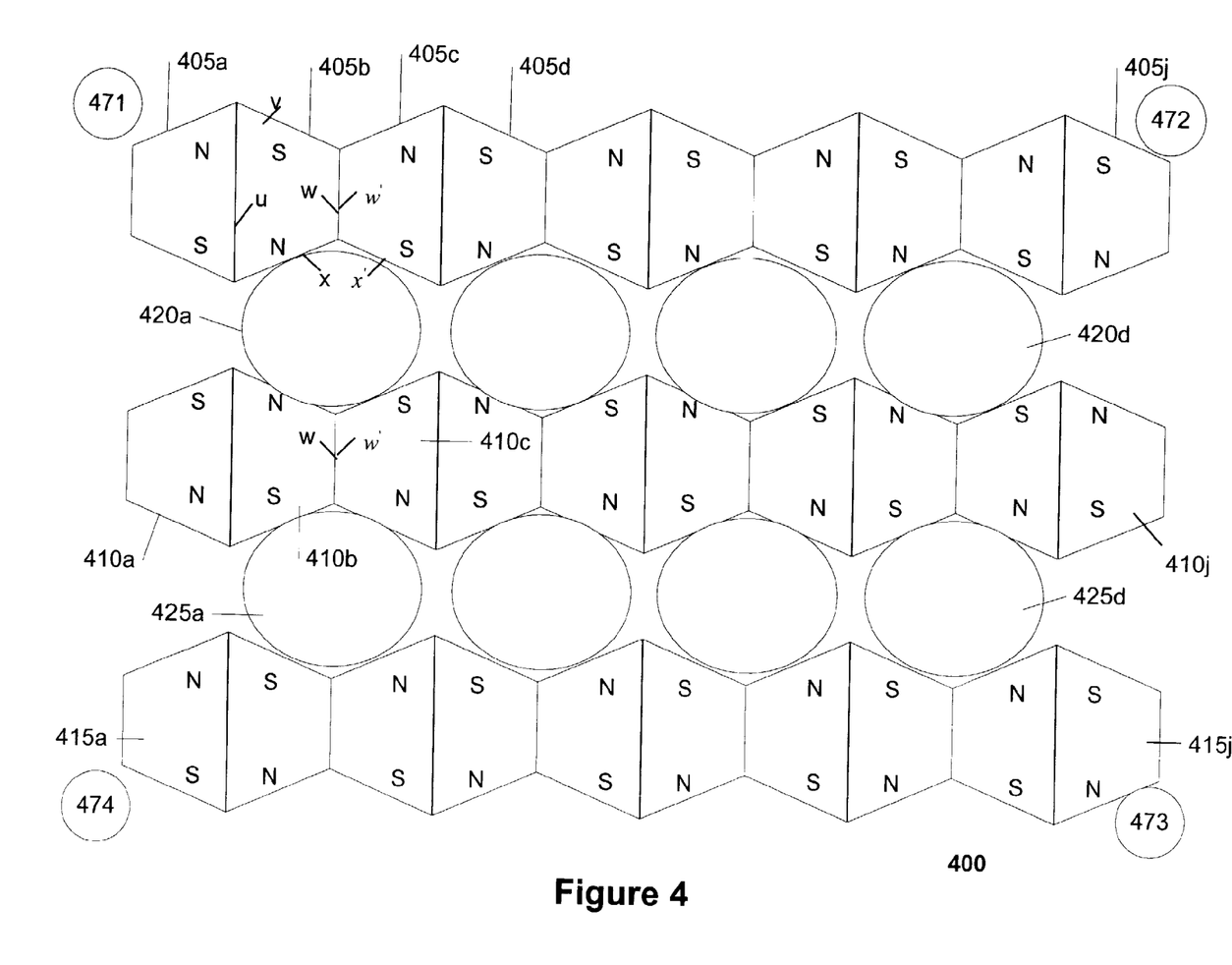
FIG. 4 illustrates a plan view of one embodiment of the invention for separation of particles in containers.

FIG. 4 presents one embodiment for an improved magnet arrangement 400 that significantly increases the strength of the magnetic fields within the wells and hence significantly increases the throughput for micro-bead separation. Although three rows of magnets with two rows for containers are illustrated, the invention contemplates a magnet arrangement 400 comprising any number of magnets with any number of rows for containers. In FIG. 4 a number of magnets e.g., permanent magnets each having a trapezoidal shape, a trapezoidal shape being defined as a quadrilateral with at least one pair of parallel sides, are arranged in substantially parallel rows 405a–j, 410 a–j and 415a–j. In one embodiment, the magnetic arrangement 400 may be mounted on a frame, to provide rigidity for magnetic arrangement 400. In between the substantially parallel rows of trapezoidal shaped permanent magnets are disposed substantially parallel means 420a–d, and 425a–d for housing containers (hereafter housing means) with micro-beads. The substantially parallel housing means may include shallow depressions, wells, gripping means, or even openings.

In other embodiments the magnetic arrangement 400 may be raised or lowered by way of locking mechanisms and rails 471–474 perpendicular to the plane of the frame. Thus, the height of the magnetic arrangement 400 may be controlled, for example, to remove micro-beads suspended at various depths in fluids of various viscosities in the containers.

In one embodiment, the frame and the containers are made of non-permeable materials, for example, aluminum, berillium copper, glass, or plastic.

Although FIG. 4 illustrates a magnetic arrangement 400 using trapezoidal shaped magnets with a pair of parallel sides, other embodiments may include parallelogram shaped magnets with two pair of parallel sides. Embodiments of this configuration will be discussed below with reference to FIG. 7. Although the invention is disclosed using permanent magnets, other magnets including but not limited to, electro magnets may also be used so long as the magnetic field pattern is similar to the field pattern of the permanent magnets.

FIG. 4 illustrates one embodiment wherein trapezoidal shaped magnets 405b and 405c are arranged such that the parallel side w of trapezoidal shaped magnet 405b is substantially in contact with parallel side w' of adjacent trapezoidal shaped magnet 405c to form a minor junction. Also, parallel side u of trapezoidal shaped magnet 405b is substantially in contact with parallel side u' of adjacent trapezoidal shaped magnet 405a to form a major junction. Leg x of trapezoidal magnet 405b and leg x of adjacent trapezoidal magnet 405c form an angle θ with respect to each other, each leg being tangential to the circumference of housing means 420a. It will be appreciated by one skilled in the art that the angle θ formed by legs x and x of trapezoidal shaped magnets 405b and 405c may be dependent upon the shape of housing means 420a. For example, for a housing means with an oval shape with the major axis of the oval approximately collinear with junction w w', angle θ will be smaller as compared with the angle for a housing means with a circular shape.

As illustrated in FIG. 4, the north-south magnetic fields of the trapezoidal shaped magnets in each row are substantially coplanar with a transverse cross sectional view of magnetic arrangement 400. In a given row, each trapezoidal shaped magnet's north-south field direction alternates with the north-south field direction of the adjacent trapezoidal shaped magnet. Thus, the north-south fields of trapezoidal shaped magnets 405b and 405c are coplanar with the transverse cross section view of magnetic arrangement 400, and have a north-south field orientation substantially parallel with each other. However, the north-south field direction of magnet 405b is approximately 180 degrees out of phase with the direction of the north-south field of adjacent trapezoidal shaped magnet 405c.

Similarly, trapezoidal shaped magnets 410b and 410c, located opposite trapezoidal shaped magnets 405b and 405c respectively, have north-south fields that are coplanar with the transverse cross sectional view of magnetic arrangement 400. Trapezoidal shaped magnets 410b and 410c have a north-south magnetic field orientation substantially parallel with each other, with north-south magnetic field directions 180 degrees out of phase with respect to each other. However, the north-south magnetic field direction of magnets in any given row opposes the north-south magnetic field direction of corresponding magnets in adjacent rows. Thus, the north-south magnetic field direction of trapezoidal shaped magnets 405b and 405c opposes the north-south magnetic field direction of trapezoidal shaped magnets 410b, and 410c respectively.

The magnetic arrangement 400 described above introduces a magnetic gradient across the diameter of each housing means, and hence across each container placed within the housing means. Thus, the magnitude of the magnetic field at the center of a container placed in a housing means is near its minimum value, and increases linearly to near its maximum value at either end of the container. Thus, for housing means 420a, the magnitude of the magnetic fields are maximum in the areas disposed near junctions w w' formed by trapezoidal shaped magnet pair 405b and 405c, and by trapezoidal shaped magnet pair 410b and 410c. Micro-beads, therefore, accumulate along the sides of the container where the magnetic fields are near their maximum values. By having the magnetic fields aligned as described above, large gradients, due to stronger magnetic fields, are created. The stronger magnetic fields cause the micro-beads to accumulate at a quicker rate at the sides of the container, thereby significantly increasing the throughput of micro-bead separation. In one embodiment, the strength of the magnetic field associated with a particular magnet in magnetic arrangement 400, is substantially equal to the strength of the magnetic field associated with any other magnet in the arrangement. This causes the gradients across each container to be substantially uniform, thereby collecting a substantially equal number of micro-beads near junctions w w' in the containers.

The magnets in magnetic arrangement 400 shown in FIG. 4 may be made of materials for permanent magnets known in the art such as, but not limited to, ferromagnetic, ferrimagnetic, Alinco, polymer-bonded, rare earth, and ceramic materials. In one embodiment, these magnets may have a protective cladding.

Figure 5:
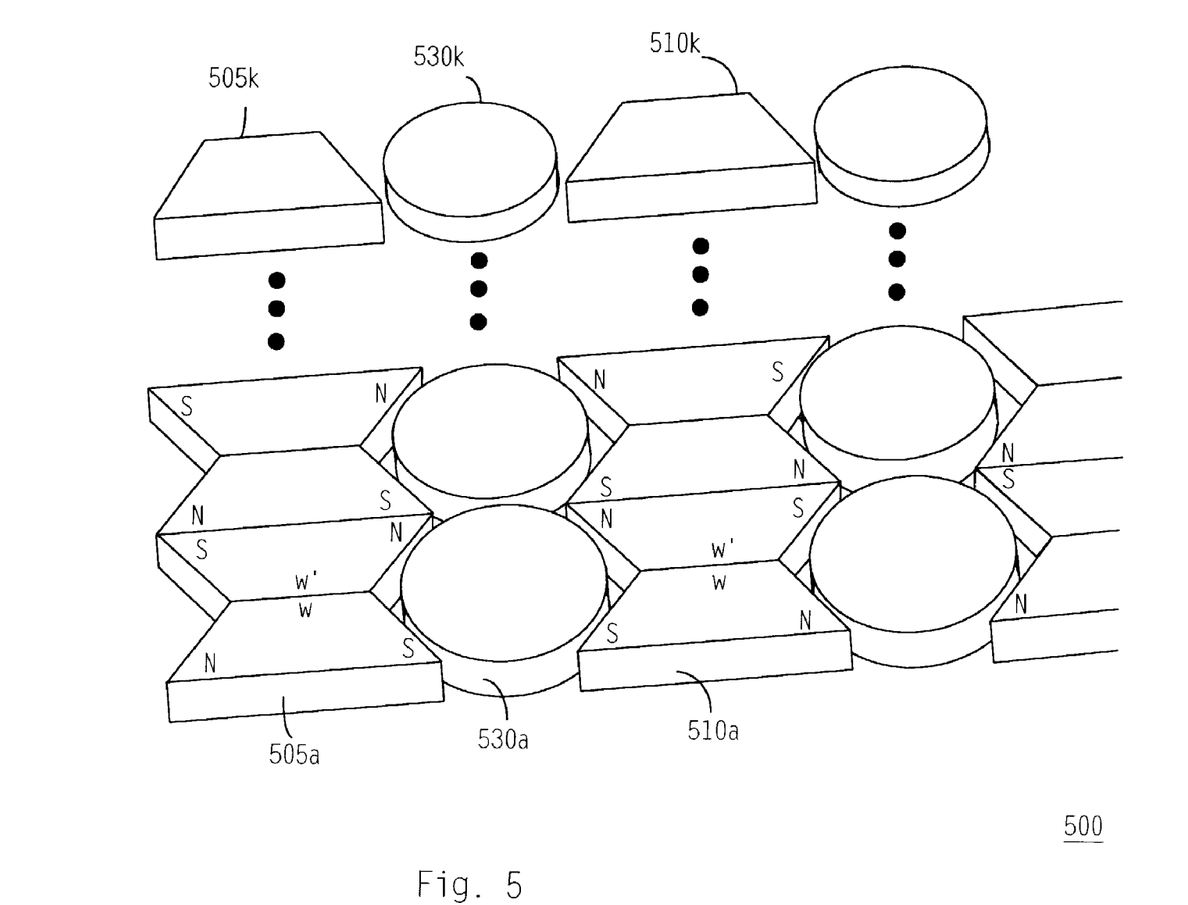
FIG. 5 illustrates a perspective view of one embodiment of the invention for separation of particles in containers.

FIG. 5 illustrates a perspective view of one embodiment of the invention for an improved arrangement of magnets facilitating separation of particles across multi-well microplates. As illustrated in FIG. 5, trapezoidal shaped magnets 505a–k and 510a–k are disposed in rows on either side of a row of wells 530a–k. The transverse cross section of the row of wells are coplanar with the rows of trapezoidal shaped magnets. In a given row, for example, row 505a–k the magnets are arranged in a plane with the north-south poles of the trapezoidal shaped magnets alternating with the north-south poles of the adjacent trapezoidal shaped magnet. The north-south poles of the trapezoidal shaped magnets in the next row, i.e., row 510a–k are oriented opposing the north-south poles of the corresponding trapezoidal shaped magnets in row 505a–k. This magnetic arrangement sets up an opposing field across the diameter of each well in the micro-plate.

The magnitude of the magnetic field at the center of each well is near its minimum value, and increases linearly to near its maximum value at either end of the well. Thus for well 530a, the magnitudes of the magnetic fields are maximum in the areas disposed near junctions w w' formed by trapezoidal shaped magnet pair 505a and 505b and by trapezoidal shaped magnet pair 510a and 510b. Micro-beads are collected in the wells in areas corresponding with maximum magnetic field strength, i.e., at areas near the junctions w w' as illustrated. The improved arrangement of magnets 500 significantly increases the throughput associated with the magnetic separation of micro-beads.

Figure 6:
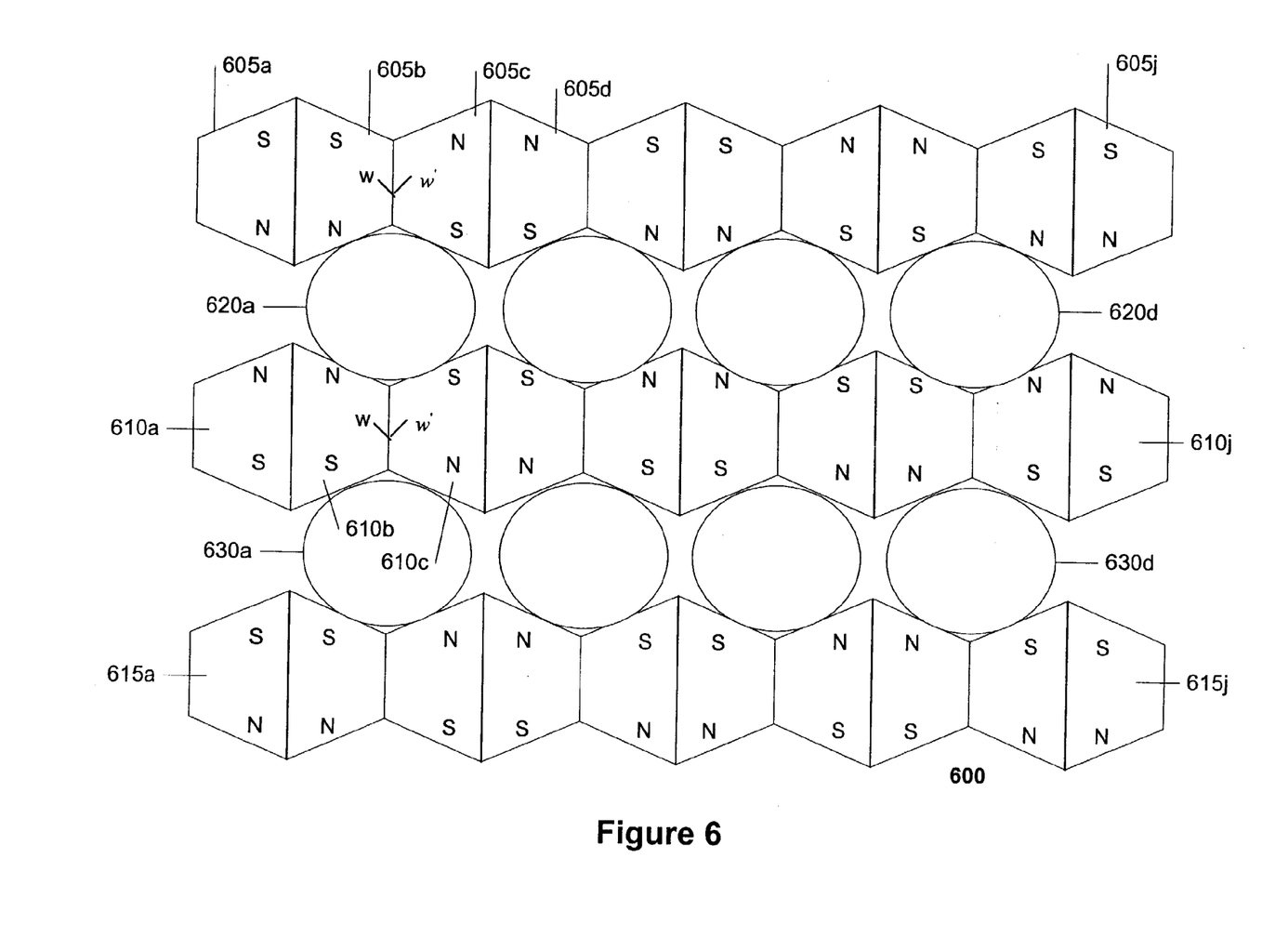
FIG. 6 illustrates a plan view of one embodiment of the invention comprising trapezoidal shaped magnets for separation of particles in containers.

FIG. 6 illustrates a plan view of one embodiment of the invention wherein rows of trapezoidal shaped magnets 605a–j, 610a–j, and 615a–j are coplanar with a transverse cross section of rows of wells 620a–d and 630a–d. As illustrated in FIG. 6, for a particular row of magnets, the north-south fields of each pair of trapezoidal shaped magnets are oriented in approximately the same direction, but alternate approximately 180 degrees with the north-south field of the adjacent pair of trapezoidal shaped magnets. Thus, for trapezoidal shaped magnets 605a, 605b, 605c, and 605d, trapezoidal shaped magnet pair 605a and 605b, and pair 605c and 605d have their north-south fields oriented in the same direction with respect to each other. However, the pair of trapezoidal shaped magnets 605c and 605d have their pair of north-south fields oriented 180 degrees out of phase with the north-south field direction of trapezoidal shaped magnet pair 605a and 605b.

The trapezoidal shaped magnets in row 605a–j have their north-south field direction opposing the corresponding north-south field direction of trapezoidal shaped magnets in row 610a–j. Magnetic arrangement 600 described above causes a magnetic gradient across the diameter of each well. Thus, the magnitude of the magnetic field at the center of each well is near its minimum value, and increases linearly to near its maximum value at either side of the well. Thus, for well 620a the magnitude of the magnetic fields are maximum in the areas disposed near junctions w w' formed by trapezoidal shaped magnet pair 605b and 605c, and by trapezoidal shaped magnet pair 610b and 610c.

Figure 7:
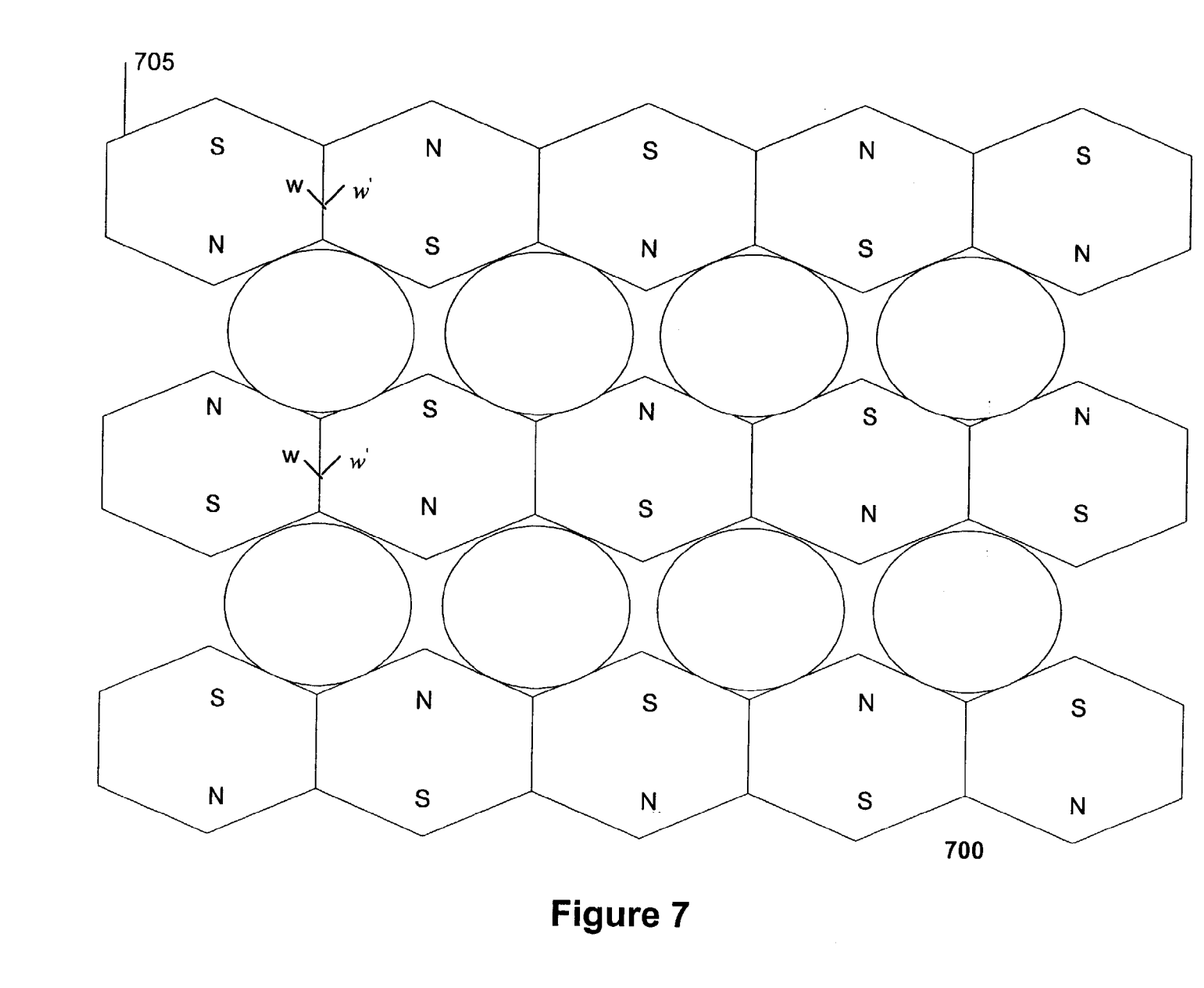
FIG. 7 illustrates a plan view of one embodiment of the invention comprising hexagonal shaped magnets for separation of particles in containers.

Although the embodiment of FIG. 6 is described using trapezoidal shaped magnets, one skilled in the art will appreciate that hexagonal shaped magnets as illustrated in FIG. 7 may alternately be used. The use of hexagonal shaped magnets facilitates the assembly and manufacture of the magnetic arrangement 700, since each pair of trapezoidal shaped magnets, e.g., trapezoidal shaped magnet pair 605a and 605b may be replaced with a single hexagonal shaped magnet 705.

Figure 8:
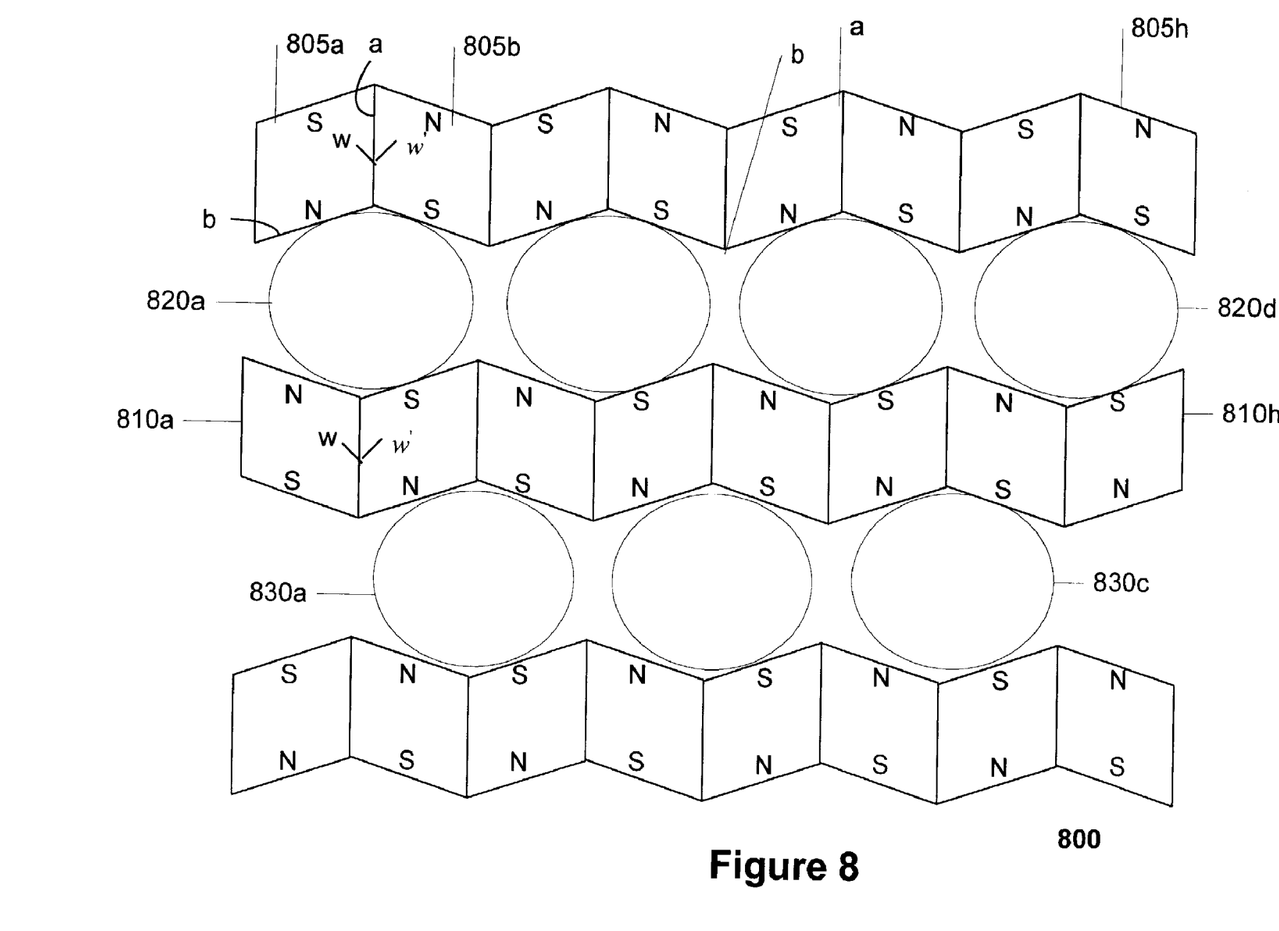
FIG. 8 illustrates a plan view of an embodiment of the invention comprising parallelogram shaped magnets for separation of particles in containers.

FIG. 8 illustrates a plan view of an embodiment of the invention comprising rows of parallelogram shaped magnets 805a–h, 810a–h, and 815a–h. In one embodiment, as illustrated in FIG. 8 two opposing angles a and b of each parallelogram have values of less than ninety degrees. Rows of wells 820a–d, and 830a–d are disposed between rows of the parallelogram shaped magnets. As illustrated in FIG. 8, the north-south magnetic field of each parallelogram shaped magnets in a row are substantially coplanar with a transverse cross sectional view of the rows of wells. In a given row, each parallelogram shaped magnet's north-south field direction alternates approximately 180 degrees with the north-south field direction of the adjacent parallelogram shaped magnet. Thus, parallelogram shaped magnet 805a has a magnetic field that is oriented approximately 180 degrees out of phase with adjacent parallelogram shaped magnet 805b. However, as described earlier, the north-south magnetic field direction of parallelogram shaped magnets in row 810a–h opposes the north-south magnetic field direction of corresponding parallelogram shaped magnets in row 805a–h.

The magnetic arrangement 800 described above causes a magnetic gradient across the diameter of each well. Thus, the magnitude of the magnetic field at the center of each well is near its minimum value and increases linearly to near its maximum value at either end of the well. Thus, for well 820a the magnitudes of the magnetic fields are maximum in the areas disposed near junctions w w' formed by parallelogram shaped magnet pair 805b and 805c and by parallelogram shaped magnet pair 810b and 810c. Micro-beads, therefore, accumulate along the sides of the wells at positions where the magnetic fields are near their maximum values. By having the magnetic fields aligned as described above, a significant increase in the throughput of magnetic separation of micro-beads is realized.

In general, those skilled in the art will recognize that the invention is not limited by the details described, instead, the invention can be practiced with modifications and alterations within the spirit and scope of the appended claims. The description is thus to be regarded as illustrative instead of restrictive on the invention.

Thus, an improved arrangement of magnets, in particular, poles of the magnets, for consistent separation of particles in a solution across a container has been described.

What is claimed is:

1. A magnetic separation apparatus comprising:
   a plurality of magnets arranged in a first row and in a second row on a frame, wherein the plurality of magnets are oriented in a plane coplanar with a horizontal cross sectional plane of the frame; and housing means between the first row and the second row for housing containers, wherein the plurality of magnets apply north-south magnetic fields oriented coplanar with the horizontal cross sectional plane of the frame, wherein the north-south magnetic field direction of a first magnet in the first row alternates 180 degrees from the north-south magnetic field direction of a second magnet in the first row, and the north-south magnetic field direction of a first magnet in the second row opposes the north-south magnetic field direction of the first magnet in the first row.

2. An apparatus as in claim 1 wherein the housing means houses a row of containers.

3. An apparatus as in claim 2 wherein the plurality of magnets comprises a plurality of trapezoidal shaped magnets.

4. An apparatus as in claim 3 further comprising:

a first parallel side of a first trapezoidal shaped magnet substantially in contact with a first parallel side of a second trapezoidal shaped magnet to form a minor junction; and a second larger parallel side of the first trapezoidal magnet substantially in contact with a second larger parallel side of a third trapezoidal magnet to form a major junction.

5. An apparatus as in claim 4 wherein each container in the row of containers is substantially aligned about the minor junction.

6. An apparatus as in claim 2 wherein the plurality of magnets comprises a plurality of hexagonal shaped magnets.

7. An apparatus as in claim 2 wherein the plurality of magnets comprises a plurality of parallelogram shaped magnets.

8. An apparatus as in claim 2, wherein the row of containers comprises a multi-well micro-plate.

9. An apparatus as in claim 8, wherein the multi-well micro-plate comprises at least one of a 96-well micro-plate, a 384-well micro-plate, and a 1536-well micro-plate.

10. An apparatus as in claim 2, wherein the row of containers comprises at least one of a substantially cylindrical tube, a substantially square tube, a vial, a Petri dish, a pipette, and a bottle.

11. An apparatus as in claim 2 further comprising means for raising the frame to apply the north-south magnetic fields at different heights of the containers.

12. An apparatus as in claim 1, wherein the plurality of magnets comprises a plurality of magnets encased within a protective housing.

13. An apparatus as in claim 1, wherein the plurality of magnets comprises at least one of a plurality of permanent magnets and a plurality of electromagnets.

14. A method for magnetic separation comprising:

arranging a plurality of magnets in a first row and in a second row on a frame, wherein the plurality of magnets are oriented in a plane coplanar with a horizontal cross sectional plane of the frame;

receiving, in a row of containers, between the first row and the second row a plurality of particles along with a plurality of magnetically susceptible particles;

separating the magnetically susceptible particles from the plurality of particles when the plurality of magnets apply north-south magnetic fields oriented coplanar with the horizontal cross sectional plane of the row of containers, wherein the north-south magnetic field direction of a first magnet in the first row alternates 180 degrees from the north-south magnetic field direction of an adjacent magnet in the first row, and wherein the north-south magnetic field direction of a first magnet in the second row opposes the north-south magnetic field direction of the first magnet in the first row.

15. A method as in claim 14, wherein the plurality of magnets comprises a plurality of trapezoidal shaped magnets.

16. A method as in claim 15, wherein arranging a plurality of magnets comprises:

setting a first parallel side of a first trapezoidal shaped magnet substantially in contact with a first parallel side of a second trapezoidal shaped magnet to form a minor junction; and setting a second larger parallel side of the first trapezoidal magnet substantially in contact with a second larger parallel side of a third trapezoidal magnet to form a major junction.

17. A method as in claim 16, wherein each container in the row of containers is substantially aligned about the minor junction.

18. A method as in claim 14, wherein the plurality of magnets comprises a plurality of hexagonal shaped magnets.

19. A method as in claim 14, wherein the plurality of magnets comprises a plurality of parallelogram shaped magnets.

20. A method as in claim 14, wherein the row of containers comprises a multi-well micro-plate.

21. A method as in claim 20, wherein the multi-well micro-plate comprises at least one of a 96-well micro-plate, a 384-well micro-plate, and a 1536-well micro-plate.

22. A method as in claim 14, wherein the row of containers comprises at least one of a substantially cylindrical tube, a substantially square tube, a vial, a Petri dish, a pipette, and a bottle.

23. A method as in claim 14, wherein the plurality of magnets comprises a plurality of magnets encased within a protective housing.

24. A method as in claim 14, wherein the plurality of magnets comprises at least one of a plurality of permanent magnets and a plurality of electromagnets.

* * * * *